(12) United States Patent
Pi

(10) Patent No.: US 10,788,418 B2
(45) Date of Patent: Sep. 29, 2020

(54) FOOD STATE MEASURING DEVICE, FOOD STATE MEASURING MODULE, AND SMART DEVICE INCLUDING THE SAME

(71) Applicant: Do Yeon Pi, Seoul (KR)

(72) Inventor: Do Yeon Pi, Seoul (KR)

( * ) Notice: Subject to any disclaimer, the term of this patent is extended or adjusted under 35 U.S.C. 154(b) by 85 days.

(21) Appl. No.: 15/862,784

(22) Filed: Jan. 5, 2018

(65) Prior Publication Data

US 2018/0136119 A1 May 17, 2018

Related U.S. Application Data

(63) Continuation of application No. PCT/KR2016/007367, filed on Jul. 7, 2016.

(30) Foreign Application Priority Data

Jul. 8, 2015 (KR) .......................... 10-2015-0096951

(51) Int. Cl.
| | |
|---|---|
| *G01N 21/31* | (2006.01) |
| *G01N 33/02* | (2006.01) |
| *G01J 3/28* | (2006.01) |
| *G01J 3/02* | (2006.01) |
| *G01N 27/12* | (2006.01) |

(52) U.S. Cl.
CPC .............. *G01N 21/31* (2013.01); *G01J 3/027* (2013.01); *G01J 3/28* (2013.01); *G01J 3/2823* (2013.01); *G01N 27/12* (2013.01); *G01N 33/02* (2013.01)

(58) Field of Classification Search
CPC ......... G01N 33/02; G01N 21/31; G01J 3/2823
See application file for complete search history.

(56) References Cited

U.S. PATENT DOCUMENTS

| | | | |
|---|---|---|---|
| 2007/0188753 A1* | 8/2007 | Merrill ...................... | B01F 9/02 356/326 |
| 2011/0246091 A1 | 10/2011 | Fedele | |
| 2012/0100781 A1* | 4/2012 | Zhang ................... | B24B 37/013 451/6 |

(Continued)

FOREIGN PATENT DOCUMENTS

| | | |
|---|---|---|
| CN | 1737571 A | 2/2006 |
| CN | 1749734 A | 3/2006 |

(Continued)

OTHER PUBLICATIONS

Extended European Search Report issued by the European Patent Office dated Jun. 22, 2018, which corresponds to EP16821665.3-1020 and is related to U.S. Appl. No. 15/862,784.

(Continued)

*Primary Examiner* — Maurice C Smith
(74) *Attorney, Agent, or Firm* — Studebaker & Brackett PC

(57) ABSTRACT

Disclosed are a food state measuring device, a food state measuring module, and a smart device including the same. The food state measuring device includes an optical spectrum acquiring unit configured to image a food to acquire an optical spectrum of the food, a database configured to store natural optical spectrum information for at least one food or a component of a food, and a control unit configured to measure a state of the food by comparing the natural optical spectrum stored in the database and the optical spectrum acquired by the optical spectrum acquiring unit.

7 Claims, 12 Drawing Sheets

| Kind \ Type | ... | Baked beef | ... | Lettuce | Matching with $F_1$ | Type of $F_1$ | Type of $F_2$ |
|---|---|---|---|---|---|---|---|
| A | | $a_1$ | | $a_2$ | | $a_1$ | $a_2$ |
| B | | $b_1$ | | $b_2$ | | $b_1$ | $b_2$ |
| C | | $c_1$ | | $c_2$ | | $c_1$ | $c_2$ |
| D | | $d_1$ | | $d_2$ | | $d_1$ | $d_2$ |
| E | | $e_1$ | | $e_2$ | | $e_1$ | $e_2$ |

Matching with $F_2$

(56) References Cited

U.S. PATENT DOCUMENTS

| | | | |
|---|---|---|---|
| 2012/0293801 A1 | 11/2012 | Kanai et al. | |
| 2013/0229646 A1 | 9/2013 | Sakurai | |
| 2014/0309968 A1* | 10/2014 | Diezmos | G06Q 30/0278 |
| | | | 702/189 |
| 2015/0036138 A1 | 2/2015 | Watson et al. | |
| 2016/0265974 A1* | 9/2016 | Ertel | G01N 21/31 |

FOREIGN PATENT DOCUMENTS

| | | |
|---|---|---|
| CN | 101292149 A | 10/2008 |
| CN | 103278609 A | 9/2013 |
| JP | H08-029412 A | 2/1996 |
| JP | 2006-226945 A | 8/2006 |
| JP | 2007-108124 A | 4/2007 |
| KR | 10-2006-0056016 A | 5/2006 |
| WO | 2007/046280 A1 | 4/2007 |

OTHER PUBLICATIONS

International Search Report issued in PCT/KR2016/007367; dated Oct. 11, 2016.
An Office Action mailed by the State Intellectual Property Office of the People's Republic of China dated Oct. 12, 2019, which corresponds to Chinese Patent Application No. 201680040217.2 and is related to U.S. Appl. No. 15/862,784; with English language translation.

* cited by examiner

FIG. 3

| Spectrum of $F_1$ | |
|---|---|
| Wavelength | Strength |
| 0.1nm | 1 |
| 1nm | 1 |
| 300nm | 3 |
| 301nm | 3 |
| 302nm | 3 |
| 697nm | 10 |
| 698nm | 10 |
| 699nm | 10 |
| 700nm | 10 |

| Spectrum of $F_2$ | |
|---|---|
| Wavelength | Strength |
| 0.1nm | 1 |
| 1nm | 1 |
| 300nm | 10 |
| 301nm | 10 |
| 302nm | 10 |
| 697nm | 3 |
| 698nm | 3 |
| 699nm | 3 |
| 700nm | 3 |

FIG. 5

| Type \ Kind | Baked beef | Measurement result of $F_1$ | Deviation |
|---|---|---|---|
| A | $a_1$ | $a_1'$ | $da_1$ |
| B | $b_1$ | $b_1'$ | $db_1$ |
| C | $c_1$ | $c_1'$ | $dc_1$ |
| D | $d_1$ | $d_1'$ | $dd_1$ |
| E | $e_1$ | $e_1'$ | $de_1$ |

FIG. 6

| Comp. Type | $I_1$ | $I_2$ | $I_3$ | $I_4$ | ... | $I_m$ |
|---|---|---|---|---|---|---|
| A | $a\_I_1$ | | | | | $a\_I_m$ |
| B | $b\_I_1$ | | | | | $b\_I_m$ |
| C | $c\_I_1$ | | | | | $c\_I_m$ |
| D | $d\_I_1$ | | | | | $d\_I_m$ |
| E | $e\_I_1$ | | | | | $e\_I_m$ |

FIG. 7

| Comp. \ Kind | $F_1$ | $F_2$ |
|---|---|---|
| $I_1$ | 15% | 0% |
| $I_2$ | 15% | 0% |
| $I_3$ | 50% | 70% |
| $I_4$ | 20% | 30% |
| $I_5$ | 0% | 0% |

FOOD STATE MEASURING DEVICE, FOOD STATE MEASURING MODULE, AND SMART DEVICE INCLUDING THE SAME

CROSS-REFERENCE TO RELATED APPLICATIONS

The present application is a continuation of International Patent Application No. PCT/KR2016/007367, filed on Jul. 7, 2016, which is based upon and claims the benefit of priority to Korean Patent Application No. 10-2015-0096951, filed on Jul. 8, 2015. The disclosures of the above-listed applications are hereby incorporated by reference herein in their entirety.

BACKGROUND

Embodiments of the inventive concept described herein relate to a food state measuring device, a food state measuring module, and a smart device including the same.

Until now, the contents on the fresh degree or safety of foods have been identified only through the explanations of salespersons or by the naked eyes of consumers. In particular, articles of the traditional markets, which are neither packed nor provided with valid dates, depend on them more. For this reason, the consumers have fewer opportunities to purchase clean and fresh foods.

Today when the well-being cultures form one social trend, demands of the consumers to check the fresh degree of foods and select safe foods are gradually increasing.

In spite of the increasing demands of the users which desire to determine the states of the foods, such as fresh degree, devices which may be conveniently carried by the user and which may simply determine the states of the foods without contacting the foods have not been distributed.

SUMMARY

Embodiments of the inventive concept provide a food state measuring device that may accurately measure a state of a food, such as fresh degree, a food state measuring module, and a smart device including the same.

The technical objects of the inventive concept are not limited to the above-mentioned ones, and the other unmentioned technical objects will become apparent to those skilled in the art from the following description.

In accordance with an aspect of the inventive concept, there is provided a food state measuring device including an optical spectrum acquiring unit configured to image a food to acquire an optical spectrum of the food, a database configured to store natural optical spectrum information for at least one food or a component of a food, and a control unit configured to measure a state of the food by comparing the natural optical spectrum stored in the database and the optical spectrum acquired by the optical spectrum acquiring unit.

The food state measuring device may further include an output unit configured to inform a user of the state of the food measured by the control unit.

The state of the food may include at least one of the kind of the food, a food component, and a fresh degree.

The control unit may identify the kind of the food by using a first comparison result of the optical spectrum, and may identify the fresh degree of the food by using a second comparison result of the optical spectrum.

The food state measuring device may further include a memory card in which the database is realized and which is attached in the food state measuring device.

In accordance with another embodiment of the inventive concept, there is provided a food state measuring module mechanically and electrically coupled to a smart device, the food state measuring module including an optical spectrum acquiring unit configured to image a food to acquire an optical spectrum of the food, and an interface unit configured to transmit the optical spectrum acquired by the optical spectrum acquiring unit to the smart device, and wherein the smart device stores natural optical spectrum information for at least one food or a component of a food, and measures a state of the food by comparing the stored natural optical spectrum and the optical spectrum acquired by the optical spectrum acquiring unit.

In accordance with another aspect of the inventive concept, there is provided a smart device including a food state measuring module, wherein the food state measuring module includes an optical spectrum acquiring unit configured to image a food to acquire an optical spectrum of the food, a database configured to store natural optical spectrum information for at least one food or a component of a food, and a control unit configured to measure a state of the food by comparing the natural optical spectrum stored in the database and the optical spectrum acquired by the optical spectrum acquiring unit.

In accordance with another aspect of the inventive concept, there is provided food state measuring device including an optical spectrum acquiring unit configured to image a food to acquire an optical spectrum of the food, an olfactory sensor configured to detect a smell of the food, a database configured to store natural optical spectrum information for at least one food or a component of a food, and a natural smell for at least one food or a component of a food, and a control unit configured to measure a state of the food by comparing the natural optical spectrum stored in the database and the optical spectrum acquired by the optical spectrum acquiring unit or comparing the natural smell stored in the database and the smell detected by the olfactory sensor.

The control unit may primarily measure the state of the food only by using the smell comparison result.

If it is impossible to primarily measure the state of the food only by using the smell comparison result, the control unit may secondarily measure the state of the food by using only the comparison result of the optical spectrum or by using the smell comparison result and the comparison result of the optical spectrums.

Detailed items of the other embodiments are included in the detailed description and the accompanying drawings.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 3 is an exemplary view schematically illustrating optical spectrums for foods measured by using the food state measuring device according to the embodiment of the inventive concept;

FIG. 5 is an exemplary view schematically illustrating that a change of a state of a food is identified based on an optical spectrum measured by using the food state measuring device according to the embodiment of the inventive concept;

FIG. 6 is an exemplary view schematically illustrating values for types of natural spectrums for components of a food;

FIG. 7 is an exemplary view schematically illustrating components of a food measured by using the food state measuring device according to the embodiment of the inventive concept;

DETAILED DESCRIPTION

Figure 1:
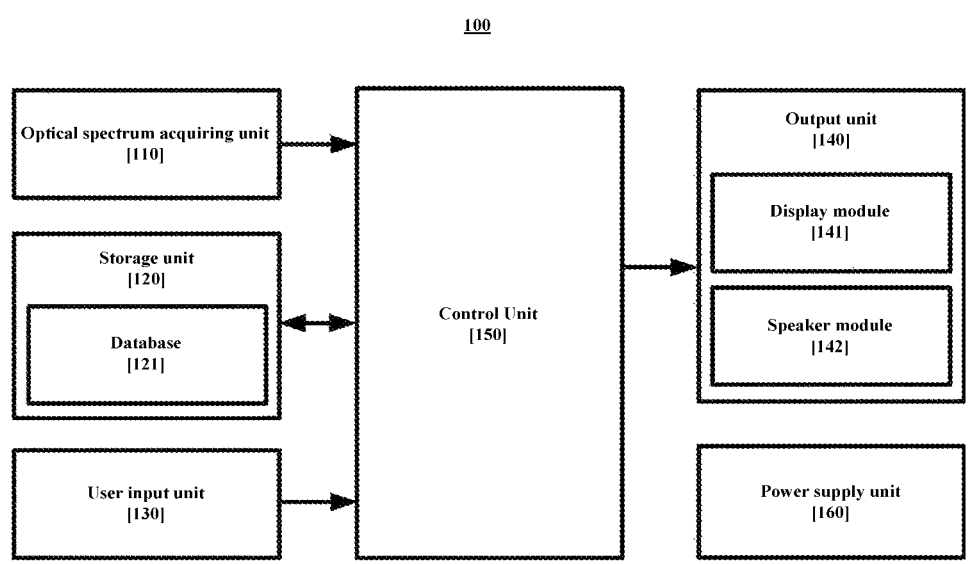
FIG. 1 is a block diagram schematically illustrating a configuration of a food state measuring device according to an embodiment of the inventive concept.

Hereinafter, exemplary embodiments of the inventive concept will be described in detail with reference to the accompanying drawings. The above and other aspects, features and advantages of the invention will become apparent from the following description of the following embodiments given in conjunction with the accompanying drawings. However, the inventive concept is not limited to the embodiments disclosed below, but may be implemented in various forms. The embodiments of the inventive concept are provided to make the disclosure of the inventive concept complete and fully inform those skilled in the art to which the inventive concept pertains of the scope of the inventive concept. The same reference numerals denote the same elements throughout the specification.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements.

Figure 2:
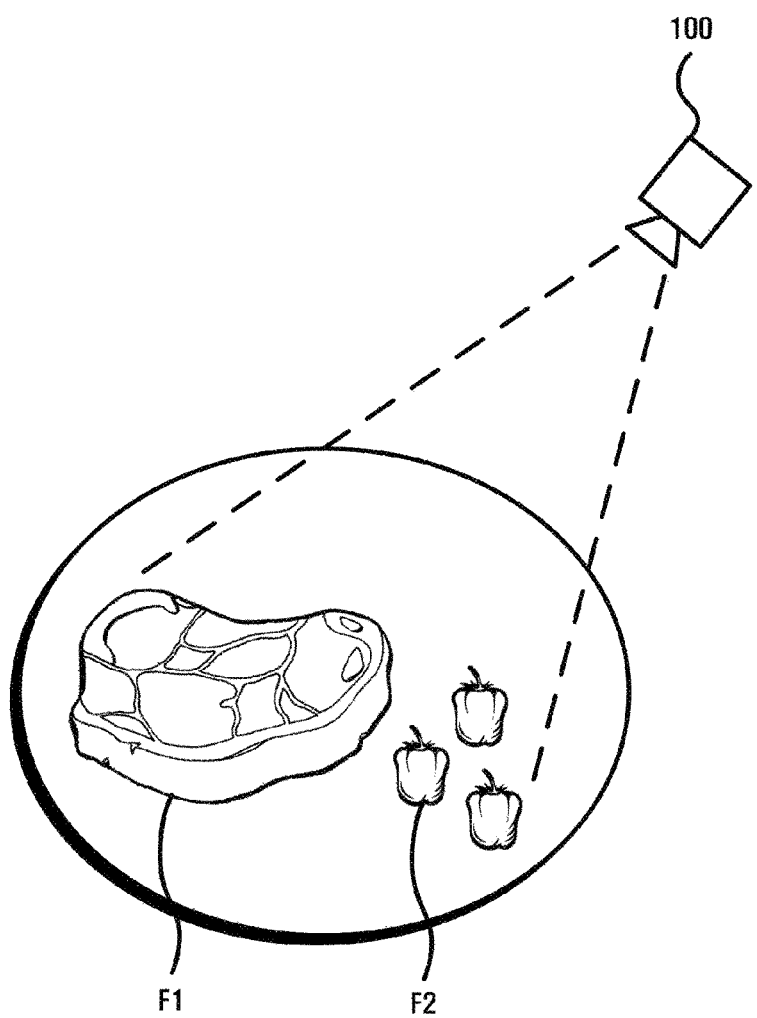
FIG. 2 is an exemplary view schematically illustrating that a food is imaged by using a food state measuring device according to an embodiment of the inventive concept.

FIG. 1 is a block diagram schematically illustrating a configuration of a food state measuring device according to an embodiment of the inventive concept. FIG. 2 is an exemplary view schematically illustrating that a food is imaged by using a food state measuring device according to an embodiment of the inventive concept.

Referring to FIG. 1, the food state measuring device 100 according to the embodiment of the inventive concept includes an optical spectrum acquiring unit 110, a storage unit 120, a user input unit 130, an output unit 140, a control unit 150, and a power supply unit 160.

The optical spectrum acquiring unit 110 images foods F1 and F2 and acquires optical spectrums for the foods. In detail, the optical spectrum acquiring unit 110 may image and obtain light reflected from an image of a food or a food and may acquire an optical spectrum for the corresponding food.

The storage unit 120 stores various data and instructions. The storage unit 120 may store system software and various applications for an operation of the food state measuring device 100. The storage unit 120 may include a random access memory (RAM), a read only memory (ROM), an erasable programmable ROM (EPROM), an electrically erasable programmable ROM (EEPROM), a flash memory, a hard disk, a detachable disk, or a computer readable recording medium in an arbitrary form, which is well known in the art to which the inventive concept pertains.

Further, the storage unit 120 may include a database 121 that stores food information. The database 121 may store natural optical spectrum information for kinds of one or more foods and components of a food. The food information stored in the database 121 may be continuously updated by using food information provided by another computer system. Further, the database 121 is realized in a memory card (not illustrated) that may be attached to the food state measuring device 100 and the user downloads new food information from anther computer system and stores the new food information so that the food information stored in the database 121 may be continuously updated. Accordingly, the accuracy and reliability of the food information stored in the database 121 may be always maintained.

The user input unit 130 receives various information from the user. The user input unit 130 may include a keypad, a button, a switch, a touchpad, or a jog wheel. When the touch pad forms a mutual layer structure with the display module 141, a touch screen may be constituted.

The output unit 140 notifies the user of various information. The output unit 140 may output information in the form of a text, an image, or a voice. To achieve this, the output unit 140 may include a display module 141 and a speaker module 142. The display module 141 may be provided in the form such as a plasma display panel (PDP), a liquid crystal display (LCD), a thin film transistor (TFT) LCD, an organic light emitting diode (OLED), a flexible display, a 3D display, or an e-ink display, or a form that are well known in the art to which the inventive concept pertains. The output unit 140 may further include an output unit that is well known in the art to which the inventive concept pertains.

The control unit 150 controls an overall operation of the food state measuring device 100 by controlling other elements. The control unit 150 may perform the system software and the various applications stored in the storage unit 120. The control unit 150 may receive the optical spectrum information acquired by the optical spectrum acquiring unit 110, and may measure a state of the food by comparing the natural optical spectrum stored in the database 121 and the optical spectrum acquired by the optical spectrum acquiring unit 110. The state of the food measured by using the optical spectrum may include the kind of the food, the component of the food, and a fresh degree of the food. The control unit 150 may inform the user of the information on the state of the food measured according to the optical spectrum acquired by the optical spectrum acquiring unit 110 or the comparison result of the optical spectrums through the output unit 140.

The power supply unit 160 supplies electric power that is necessary for operations of the optical spectrum acquiring unit 110, the storage unit 120, the user input unit 130, the output unit 140, and the control unit 150. The power supply unit 160 may include an embedded battery.

Meanwhile, the functional blocks illustrated in FIG. 1 are merely exemplary to explain the embodiment of the food state measuring device of the inventive concept, and should be construed that some of the functional blocks illustrated in FIG. 1 may be omitted from the food state measuring device or new functional blocks (not illustrated) are added to the food state measuring device.

FIG. 3 is an exemplary view schematically illustrating optical spectrums for foods measured by using the food state measuring device according to the embodiment of the inventive concept.

Referring to FIG. 3, exemplary optical spectrums of a first food F1 and a second food F2 are illustrated. The first food F1 and the second food F2 may have different optical spectrums. In detail, an intensity of light of a long wavelength band (exemplified around about 700 nm) may be about 10 and may be predominant as compared with other bands in the optical spectrum of the first food F1, and an intensity of light of a middle band (exemplified around about 300 nm) may be about 10 and may be predominant as compared with other bands in the optical spectrum of the second food F2. That is, the foods may have different natural optical spectrums, and the food state measuring device 10 may identify the kind of the food by analyzing the optical spectrum.

Figure 4:
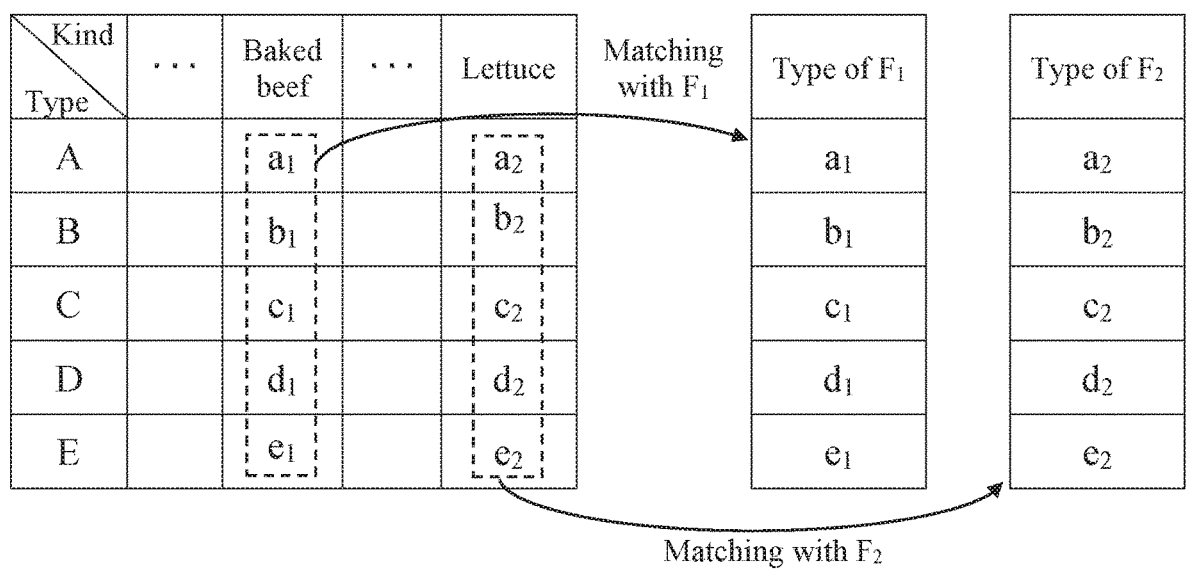
FIG. 4 is an exemplary view schematically illustrating that a kind of a food is identified based on an optical spectrum measured by using the food state measuring device according to the embodiment of the inventive concept.

FIG. 4 is an exemplary view schematically illustrating that a kind of a food is identified based on an optical spectrum measured by using the food state measuring device according to the embodiment of the inventive concept.

In FIG. 4, "a type" means values that may characterize natural optical spectrums of the foods. For example, the type may include values, such as at which wavelength band of the optical spectrum the intensity of the light is predominant, how the optical spectrum changes as the wavelength increases or decreases, how the entire intensity of the optical spectrum is, or how an average intensity for wavelength bands of the optical spectrum is, but the inventive concept is not limited thereto.

Hereinafter, in order to explain the embodiment of the food state measuring device of the inventive concept, an average intensity of light for wavelength bands of the optical spectrum as types A, B, C, D, and E of the optical spectrum will be described. In FIG. 4, type A means an average intensity of the light of the measured shortest wavelength band, type E means an average intensity of the light of the measured longest wavelength band, and types B, C, and D mean average intensities for wavelength bands between type A and type E.

The left table of FIG. 4 regarding types and kinds may be provided in the database 121 of the food state measuring device 100.

The values for the types of the optical spectrum of the first food F1 may be "a1, b1, c1, d1, and e1", and this may be compared with and matched with the values for the types of the optical spectrum of "baked beef" stored in the database 121 of the food state measuring device 100.

Likewise, the values for the types of the optical spectrum of the second food F2 may be "a2, b2, c2, d2, and e2", and this may be compared with and matched with the values for the types of the optical spectrum of "cabbage" stored in the database 121 of the food state measuring device 100.

Accordingly, the food state measuring device 100 may identify the kind of the first food F1 as baked beef, and may identify the kind of the second food F2 as cabbage.

FIG. 5 is an exemplary view schematically illustrating that a change of a state of a food is identified based on an optical spectrum measured by using the food state measuring device according to the embodiment of the inventive concept.

As described with reference to FIG. 4, the kind of the first food F1 may be automatically determined by using the optical spectrum of the first food F1 or the user may directly input the kind of the first food F1 that is a measurement target.

Referring to FIG. 5, the values for the types of the optical spectrums of the baked beef stored in the database 121 of the food state measuring device 100 may be "a1, b1, c1, d1, and e1", and the values for the types of the optical spectrums of the first food F1 may be "a1', b1', c1', d1', and e1'". The deviations of the values for the types of the optical spectrums of the baked beef and the deviations of the values for the types of the optical spectrums of the first food F1 may be "da1, db1, dc1, dd1, and de1". The deviations of the optical spectrums may represent a state change of the food, and the food state measuring device 100 may identify the state change of the food by analyzing the deviations of the optical spectrums. That is, as the deviation of the optical spectrums becomes larger, it may be identified that the state change of the food is large, for example, the fresh degree of the food is low. The deviation may be a value that is sufficiently small enough to match the kind of the food in FIG. 4.

Meanwhile, the method for identifying the state change of the food is merely exemplary, and the inventive concept may use a determination equation including various factors for determining a state of the food, for example, the fresh degree of the food as well as the magnitude of the deviation in order to identify the state change of the food, for example, the change of the fresh degree more precisely.

FIG. 6 is an exemplary view schematically illustrating values for types of natural spectrums for components of a food. FIG. 7 is an exemplary view schematically illustrating components of a food measured by using the food state measuring device according to the embodiment of the inventive concept.

Referring to FIG. 6, the natural optical spectrums for the components of the food and the values for the types of the optical spectrums may be provided in the database 121 of the food state measuring device 100. The components of the food, for example, may include protein, fat, carbohydrates, and other inorganic materials. The values for the types of the optical spectrums of a first component I1 may be "a_I1, b_I1, c_I1, d_I1, and e_I1", and the values for the types of the optical spectrums of a m-th component Im may be "a_Im, b_Im, c_Im, d_Im, and e_Im".

The optical spectrum of the food including two or more food components may linearly overlap shared optical spectrums on the food components or may nonlinearly overlap shared optical spectrums on the food components to be interpreted through a determination equation.

The values for the types of the optical spectrums of the food including two or more food components, for example, may be compared with and matched with the values for the types of the optical spectrums of two or more food components stored in the database 121 (by using a weight).

Accordingly, the food state measuring device 100 may identify the components of the food that is to be measured, and may identify a ratio of the food components by using the weight.

As illustrated in FIG. 7, the first food F1 and the second food F2 may have different components. For example, the first component I1 is fat, the second component I2 is protein, the third component I3 is moisture, the fourth component I4 is an inorganic material, and the fifth component I5 may be a toxic material.

The food state measuring device 100 may measure the contents of the components of the food, and may measure a nutritive value of the food based on the contents. Further, the food state measuring device 100, for example, may recognize whether the corresponding food contains a unique toxic material that may be generated when the food loses the freshness.

Figure 8:
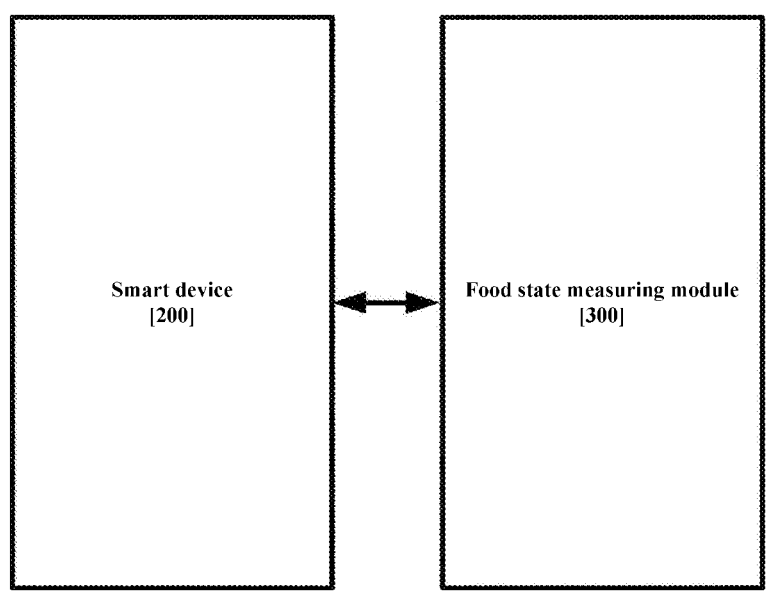
FIG. 8 is a block diagram schematically illustrating a system including a food state measuring device and a smart device according to an embodiment of the inventive concept.
Figure 9:
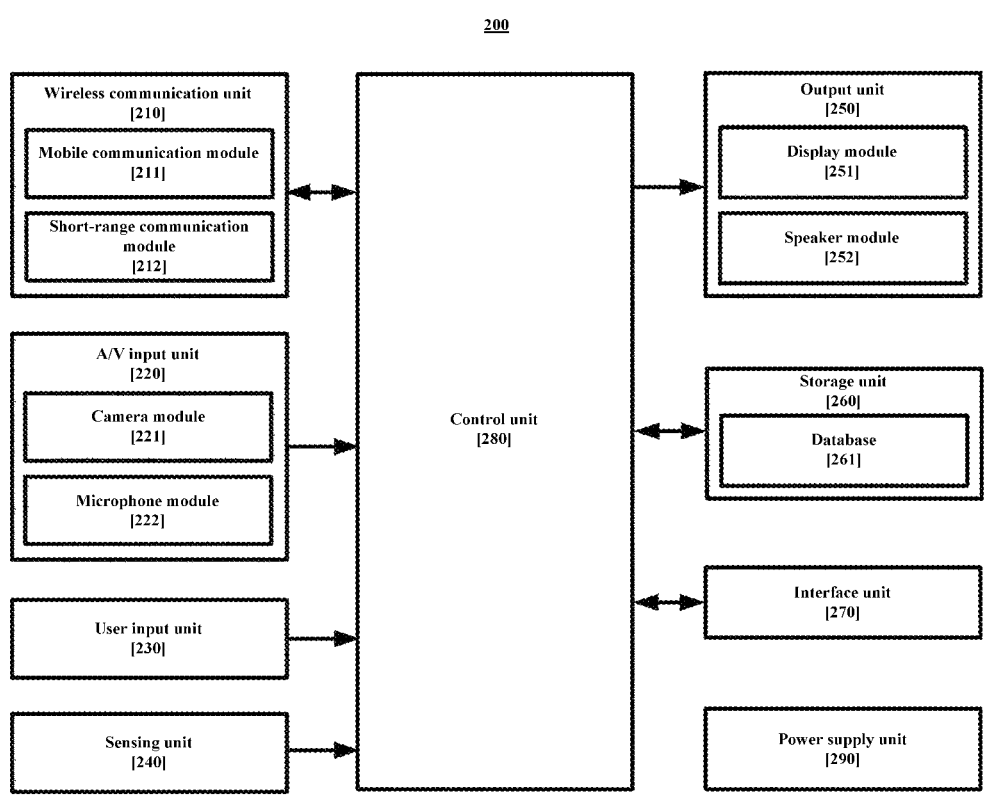
FIG. 9 is a block diagram schematically illustrating the smart device of FIG. 8.
Figure 10:
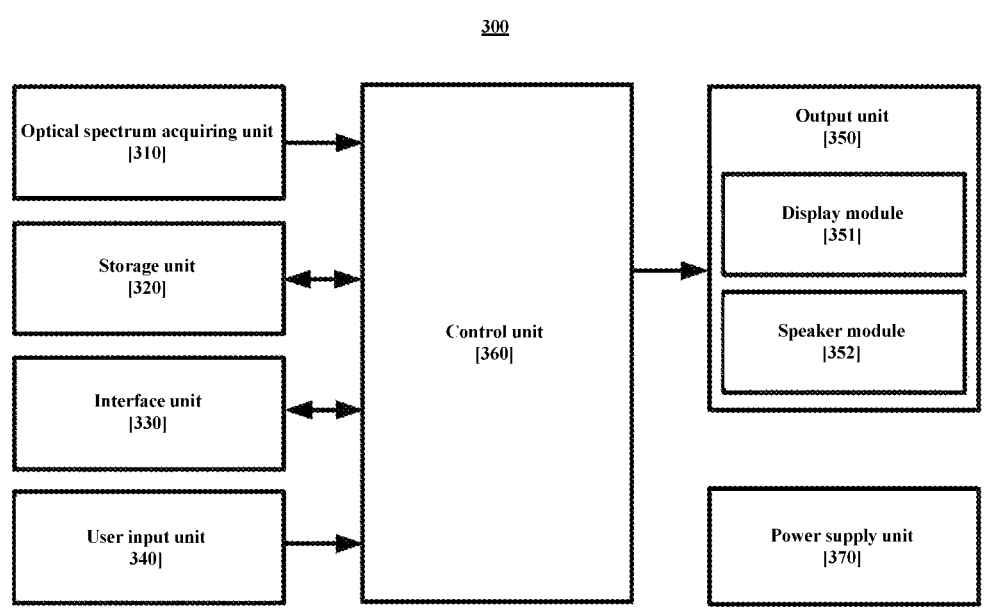
FIG. 10 is a block diagram schematically illustrating the food state measuring module of FIG. 8.

FIG. 8 is a block diagram schematically illustrating a system including a food state measuring device and a smart device according to an embodiment of the inventive concept. FIG. 9 is a block diagram schematically illustrating the smart device of FIG. 8. FIG. 10 is a block diagram schematically illustrating the food state measuring module of FIG. 8.

The embodiment illustrated in FIG. 8 is different from the embodiment described with reference to FIG. 1 in that the state of the food is measured by the smart device 200 and the optical spectrums for measuring the state of the food is acquired by the food state measuring module 300. For convenience of description, configurations that are substantially the same as those of the embodiment described with reference to FIG. 1 will not be repeated.

Referring to FIG. 8, the smart device 200 and the food state measuring module 300 may be mechanically and electrically coupled to each other. The smart device 200 refers to a computer system that may be used by the user while being carried. For example, the smart device 200 may be a computer system, such as a smartphone, a tablet, a personal digital assistant (PDA), and a laptop, and the inventive concept is not limited thereto. That is, the smart device 200 may be a specific computing system that may access to a network and that may be carried.

Referring to FIG. 9, the smart device 200 includes a wireless communication unit 210, an A/V input unit 220, a user input unit 230, a sensing unit 240, an output unit 250, a storage unit 260, an interface unit 270, a control unit 280, and a power supply unit 290.

The wireless communication unit 210 may wirelessly communicate with an external device. The wireless communication unit 210 may wirelessly communication with an external device by using mobile communication, and a wireless communication scheme, such as WiBro, Bluetooth, Wi-Fi, ZigBee, an ultrasonic wave, an infrared ray, or a radio frequency (RF). However, the wireless communication scheme of the user terminal 200 is not limited thereto. The wireless communication unit 210 may deliver data and/or information received from the external device to the control unit 280, and may transmit the data and/or information delivered from the control unit 280 to the external device. To achieve this, the wireless communication unit 210 may include a mobile communication module 211 and a short-range communication module 212.

The A/V input unit 220 is adapted to input an image or, a voice signal, and may include a camera module 221 and a microphone module 222.

The user input unit 230 receives various information from the user. The user input unit 230 may include a keypad, a button, a switch, a touchpad, or a jog wheel. When the touch pad forms a mutual layer structure with the display module 251, a touch screen may be constituted.

The sensing unit 240 detects a state of the smart device 200 or a state of the user. The sensing unit 240 may include a detection unit such as a touch sensor, a proximity sensor, a pressure sensor, a vibration sensor, a geomagnetic sensor, a gyro sensor, an acceleration sensor, or a biometric sensor. The sensing unit 240 may be used for a user input.

The output unit 250 notifies the user of various information. The output unit 250 may output information in the form of a text, an image, or a voice. To achieve this, the output unit 250 may include a display module 251 and a speaker module 252. The display module 251 may be provided in the form such as a plasma display panel (PDP), a liquid crystal display (LCD), a thin film transistor (TFT) LCD, an organic light emitting diode, a flexible display, a 3D display, or an e-ink display, or a form that are well known in the art to which the inventive concept pertains. The output unit 250 may further include an output unit that is well known in the art to which the inventive concept pertains.

The storage unit 260 stores various data and instructions. The storage unit 260 may store system software and various applications for an operation of the smart device 200. The storage unit 260 may include a random access memory (RAM), a read only memory (ROM), an erasable programmable ROM (EPROM), an electrically erasable programmable ROM (EEPROM), a flash memory, a hard disk, a detachable disk, or a computer readable recording medium in an arbitrary form, which is well known in the art to which the inventive concept pertains.

Further, the storage unit 260 may include a database 261 that stores food information. The database 261 may store natural optical spectrum information for kinds of one or more foods and components of a food.

The interface unit 270 functions as a passage with an external device (the foods state measuring module 300 in the embodiment of the inventive concept) connected to the smart device 200. The interface unit 270 may receive optical spectrum information from the food state measuring module 300. The interface unit 270 may transmit data and/or information to the food state measuring module 300 or supply electric power to the food state measuring module 300. The interface unit 270, for example, may include a wired/wireless headset port, a charger port, a wired/wireless data port, a memory card port, a universal serial bus (USB), a port that connects a device provided with an identification module, an audio input/output (I/O) port, or a video input/output (I/O) port.

The control unit 280 controls an overall operation of the smart device 200 by controlling other elements. The control unit 280 may perform the system software and the various applications stored in the storage unit 260. The control unit 280 may receive optical spectrum information acquired by the food state measuring module 300, and may measure the state of the food by comparing the natural optical spectrum stored in the database 261 and the optical spectrum acquired by the food state measuring module 300. The control unit 280 may inform the user of the information on the state of the food measured according to the optical spectrum acquired by the food state measuring module 300 or the comparison result of the optical spectrums through the output unit 250.

The power supply unit 290 supplies electric power that is necessary for operations of the wireless communication unit 210, the A/V input unit 220, the user input unit 230, the sensing unit 240, the output unit 250, the storage unit 260, the interface unit 270, and the control unit 280. The power supply unit 290 may include an embedded battery.

Referring to FIG. 10, as compared with the food state measuring device 100 described with reference to FIG. 1, the food state measuring module 300 according to the embodiment of the inventive concept further includes an interface unit 330 without including the database 121.

The interface unit 330 functions as a passage with an external device (the smart device 200 in the embodiment of the inventive concept) connected to the food state measuring module 300. The interface unit 330 may deliver optical spectrum information acquired by the optical spectrum acquiring unit 310 to the smart device 200. The interface unit 330 may receive data and/or information or electric power from the smart device 200 and deliver the data and/or information or the electric power to the internal elements.

Figure 11:
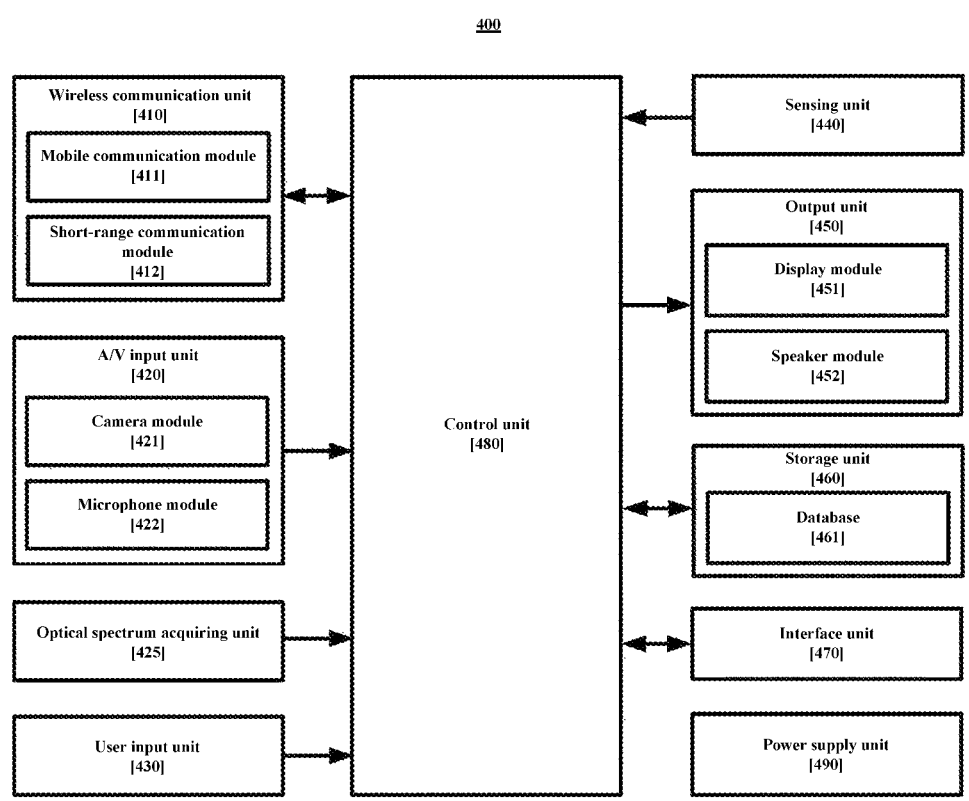
FIG. 11 is a block diagram schematically illustrating the smart device according to the embodiment of the inventive concept.

FIG. 11 is a block diagram schematically illustrating the smart device according to the embodiment of the inventive concept.

The embodiment illustrated in FIG. 11 is different from the embodiment described with reference to FIGS. 8 to 10 in that the smart device 400 further includes a food state measuring module and both the measurement of the state of the food and the acquisition of the optical spectrum for measuring the state of the food are performed by the smart device 400. For convenience of description, configurations that are substantially the same as those of the embodiment described with reference to FIG. 1 will not be repeated.

Referring to FIG. 8, the smart device 400 according to the embodiment of the inventive concept further includes a food state measuring module, and the food state measuring module may include at least an optical spectrum acquiring unit 425, a database 461, and a control unit 480.

The optical spectrum acquiring unit 425 images a food and acquires optical spectrums for the food.

The storage unit 460 may include a database 461 that stores food information. The database 461 may store natural optical spectrum information for kinds of one or more foods and components of a food.

The control unit 480 may measure a state of a food by comparing a natural optical spectrum stored in the database 461 and an optical spectrum acquired by the optical spectrum acquiring unit 425. The state of the food measured by using the optical spectrum may include the kind of the food, the component of the food, and a fresh degree of the food. The control unit 480 may inform the user of the information on the state of the food measured according to the optical spectrum acquired by the optical spectrum acquiring unit 425 or the comparison result of the optical spectrums through the output unit 450.

Figure 12:
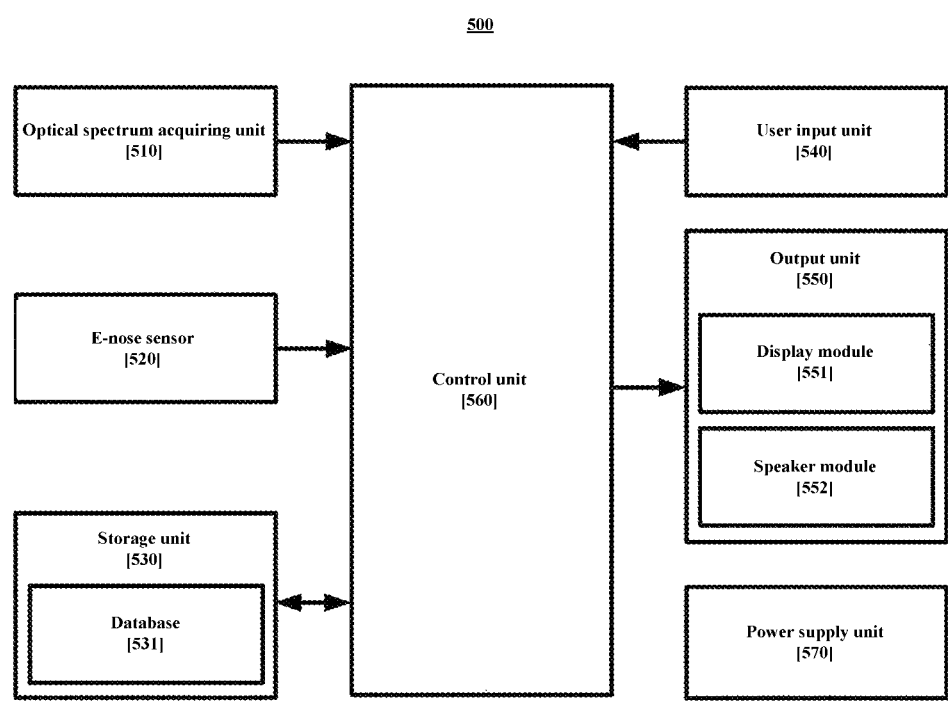
FIG. 12 is a block diagram schematically illustrating a food state measuring device according to another embodiment of the inventive concept.

FIG. 12 is a block diagram schematically illustrating a food state measuring device according to another embodiment of the inventive concept.

The embodiment illustrated in FIG. 12 is different from the embodiment described with reference to FIG. 1 in that the food state measuring device 500 further includes an E-nose sensor 520, and the state of the food is measured further by using a comparison result of smells as well as the comparison result of the optical spectrums. For convenience of description, configurations that are substantially the same as those of the embodiment described with reference to FIG. 1 will not be repeated.

Referring to FIG. 12, the food state measuring device 500 according to the embodiment of the inventive concept further includes an E-nose sensor 520.

The E-nose sensor 520 may detect a kind and a concentration (that is, a smell of the food) of a chemical in the air.

Further, the storage unit 530 may include a database 531 that stores food information. The database 531 may store natural optical spectrum information and a natural smell for kinds of one or more foods and components of a food.

The control unit 560 may measure a state of a food by comparing a natural optical spectrum stored in the database 531 and an optical spectrum acquired by the optical spectrum acquiring unit 510 or comparing a natural smell stored in the database 531 and a smell detected by the E-nose sensor 520. The state of the measured food may include the kind of the food, the component of the food, and a fresh degree of the food.

The food state measuring device 500 may measure a state of a food more accurately by further using a comparison result of a smell as well as a comparison result of an optical spectrum.

Further, the control unit 560 may primarily measure a state of a food only by using the comparison result of the smell. If the measurement is impossible, the control unit 560 may secondarily measure a state of a food only by using the comparison result of the optical spectrum or by using both the comparison result of smells and the comparison result of the optical spectrums. Accordingly, the food state measuring device 500 may measure the state of the food more accurately and more promptly.

The control unit 150 may inform the user of the information on the state of the food measured according to the optical spectrum acquired by the optical spectrum acquiring unit 510, a smell detected by the E-nose sensor 520, or the comparison result.

The method described in relation to the embodiments of the inventive concept may be implemented by a software module performed by a processor. The software module may reside in a random access memory (RAM), an ROM, an EPROM, an EEPROM, a flash memory, a register, a hard disk, a detachable disk, a CD-ROM, or a computer readable recording medium of an arbitrary form that is known in the technical field to which the inventive concept pertains.

According to the inventive concept, a state of a food, such as a fresh degree of the food, may be accurately measured while the smart device is simply carried by the user.

The aspect of the inventive concept is not limited thereto, and other unmentioned aspects of the inventive concept may be clearly appreciated by those skilled in the art from the following descriptions.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. A food state measuring device comprising:
   an imager that images a food to acquire an optical spectrum of the food;

a database configured to store natural optical spectrum information for at least one food or a component of a food; and a controller that measures a state of the food by comparing the natural optical spectrum stored in the database and the optical spectrum acquired by the imager, wherein the controller identifies components of the food based a determination whether the optical spectrum acquired by the imager is overlapped with shared optical spectrums of components stored in the database, and identifies a ratio of the identified components of the food, wherein the controller identifies the state of the food by using deviations of values for types of the optical spectrum acquired by the imager, and wherein the controller identifies that a state change of the food is larger as the deviations become larger.

2. The food state measuring device of claim 1, further comprising:

an outputter that informs a user of the state of the food measured by the controller.

3. The food state measuring device of claim 1, wherein the state of the food includes at least one of the kind of the food, a food component, and a fresh degree.

4. The food state measuring device of claim 1, wherein the controller identifies the kind of the food by using a first comparison result of the optical spectrum, and identifies the fresh degree of the food by using a second comparison result of the optical spectrum.

5. The food state measuring device of claim 1, further comprising:

a memory card in which the database is realized and which is attached in the food state measuring device.

6. A food state measurer mechanically and electrically coupled to a smart device, comprising:

an imager that images a food to acquire an optical spectrum of the food; and an interface unit configured to transmit the optical spectrum information acquired by the imager to the smart device, and wherein the smart device stores natural optical spectrum information for at least one food or a component of a food, and measures a state of the food by comparing the stored natural optical spectrum and the optical spectrum acquired by the imager, wherein the smart device identifies components of the food based a determination whether the optical spectrum acquired by the imager is overlapped with shared optical spectrums of components stored in the database, and identifies a ratio of the identified components of the food, wherein the smart device identifies the state of the food by using deviations of values for types of the optical spectrum acquired by the imager, and wherein the smart device identifies that a state change of the food is larger as the deviations become larger.

7. A smart device comprising:

a food state measurer, wherein the food state measurer includes:

an imager that images a food to acquire an optical spectrum of the food;

a database configured to store natural optical spectrum information for at least one food or a component of a food; and a controller that measures a state of the food by comparing the natural optical spectrum stored in the database and the optical spectrum acquired by the imager, wherein the controller identifies components of the food based a determination whether the optical spectrum acquired by the imager is overlapped with shared optical spectrums of components stored in the database, and identifies a ratio of the identified components of the food, wherein the controller identifies the state of the food by using deviations of values for types of the optical spectrum acquired by the imager, and wherein the controller identifies that a state change of the food is larger as the deviations become larger.

* * * * *